United States Patent
Talgorn et al.

(10) Patent No.: US 11,751,810 B2
(45) Date of Patent: Sep. 12, 2023

(54) LIFTING SENSOR PATCH

(71) Applicant: KONINKLIJKE PHILIPS N.V., Eindhoven (NL)

(72) Inventors: Elise Claude Valentine Talgorn, Eindhoven (NL); Lucas Jacobus Franciscus Geurts, Best (NL); Lieven Adriaenssen, Vilvoorde (BE)

(73) Assignee: KONINKLIIKE PHILIPS N.V., Eindhoven (NL)

( * ) Notice: Subject to any disclaimer, the term of this patent is extended or adjusted under 35 U.S.C. 154(b) by 703 days.

(21) Appl. No.: 16/347,433

(22) PCT Filed: Nov. 6, 2017

(86) PCT No.: PCT/EP2017/078271
§ 371 (c)(1),
(2) Date: May 3, 2019

(87) PCT Pub. No.: WO2018/087023
PCT Pub. Date: May 17, 2018

(65) Prior Publication Data
US 2019/0261923 A1    Aug. 29, 2019

(30) Foreign Application Priority Data
Nov. 8, 2016 (EP) ..................................... 16197646

(51) Int. Cl.
*A61B 5/00* (2006.01)
*C09J 7/00* (2018.01)
(Continued)

(52) U.S. Cl.
CPC .............. *A61B 5/6833* (2013.01); *A61B 5/70* (2013.01); *C09J 7/00* (2013.01); *A61B 5/6831* (2013.01);
(Continued)

(58) Field of Classification Search
CPC ....... A61B 5/6833; A61B 5/70; A61B 5/6831; A61B 2562/245; C09J 7/00; C09J 2203/37; C09J 2301/10; Y10T 428/14
See application file for complete search history.

(56) References Cited

U.S. PATENT DOCUMENTS 4,911,563 A * 3/1990 Ciani ................. B65D 33/1691
383/89
5,824,380 A * 10/1998 Hagen ...................... B32B 3/04
383/62
(Continued)

FOREIGN PATENT DOCUMENTS

WO    2010039751 A1    4/2010
WO    2013086320 A1    6/2013

*Primary Examiner* — Patricia L. Nordmeyer

(57) ABSTRACT

The described embodiments relate to a sensor patch that can be temporarily removed and re-applied in the same location using a side element of the sensor patch. The side element can be folded onto the sensor patch when the sensor patch is adhered to an object such as an appendage of a person. The side element can be unfolded and adhered to the appendage in order to preserve the placement of the sensor patch on the appendage. In this way, maintenance such as cleaning can be performed on the area where the sensor patch is located without having to dispose of the sensor patch. Once maintenance is completed, the side element can be folded back onto a surface of the sensor patch until maintenance is to be performed again.

15 Claims, 7 Drawing Sheets

(52) U.S. Cl.
CPC ..... *A61B 2562/245* (2013.01); *C09J 2203/37* (2020.08); *C09J 2301/10* (2020.08); *Y10T 428/14* (2015.01)

(56) References Cited

U.S. PATENT DOCUMENTS

| | | | |
|---|---|---|---|
| 5,984,247 A * | 11/1999 | Luhmann | A47G 1/175 248/205.3 |
| 6,343,604 B1 | 2/2002 | Beall | |
| 6,436,500 B1 * | 8/2002 | Yingst | B65D 33/1691 383/203 |
| 6,992,232 B1 | 1/2006 | Kemeny | |
| 9,333,706 B2 * | 5/2016 | Mag | H04M 1/0262 |
| 2003/0219469 A1 | 11/2003 | Johnson et al. | |
| 2005/0033215 A1 | 2/2005 | Lebner | |
| 2008/0091133 A1 | 4/2008 | Matter | |
| 2011/0077497 A1 * | 3/2011 | Oster | A61B 5/274 600/372 |
| 2013/0178725 A1 | 7/2013 | O'Neil | |
| 2014/0243788 A1 | 8/2014 | Cantor | |
| 2016/0193005 A1 | 7/2016 | Nazari | |

* cited by examiner

LIFTING SENSOR PATCH

This application is the U.S. National Phase application under 35 U.S.C. § 371 of International Application No. PCT/EP2017/078271, filed on 6 Nov. 2017, which claims the benefit of European Application Serial No. 16197646.9, filed 8 Nov. 2016. These applications are hereby incorporated by reference herein.

FIELD OF THE INVENTION

The described embodiments are directed generally to wearable skin patches. More particularly, but not exclusively, the various systems, methods, and apparatus disclosed herein relate to a wearable sensor patch that can include a side element for securing the sensor patch in place while a portion of the sensor patch is removed for maintenance purposes.

BACKGROUND OF THE INVENTION

Wearable skin patches can be used for sports, drug-delivery, patient monitoring, or protecting a body part. In many cases, wearable patches are replaced multiple times before they are no longer necessary for a person to wear. Patch replacement is often necessitated by hygiene requirements that seek to curb incidence of infection and discomfort for users. However, replacing patches involves cost and time that can increase depending on the complexity. For medical patches, healthcare workers may not have the time to completely remove and replace numerous medical patches in a given day depending the size of the patient population they are managing. In the context of care-at-home, the users may have difficulty replacing the patch properly and at the prescribed location.

SUMMARY OF THE INVENTION

The present disclosure is directed to systems, methods, and apparatus for using a sensor patch that includes a side element for securing the sensor patch in place while maintenance of the sensor patch is performed. Generally, in one aspect, an apparatus configured with selected aspects of the present disclosure may include: an adhesive body that includes a first adhesive surface and a non-adhesive surface opposite the first adhesive surface, the first adhesive surface configured to adhere to an object; and a side element that extends from an edge of the adhesive body. In various embodiments, the side element may include a second adhesive surface that is configured to: adhere to the non-adhesive surface when in a rest mode, and adhere to the object when in a lift mode.

In various embodiments, the first adhesive surface may have a lower bond strength than the second adhesive surface. In various embodiments, the side element may include a non-adhesive portion configured to face away from the second adhesive surface when the side element is in the rest mode. In various embodiments, the non-adhesive portion may extend between the adhesive body and the second adhesive surface when the side element is in the lift mode. In various embodiments, the second adhesive surface, when in the rest mode, may be configured to fold between a first portion of the second adhesive surface and a second portion of the second adhesive surface. In various embodiments, when in the rest mode, the first portion of the second adhesive surface may adhere to the second portion of the second adhesive surface, and a distal end of the side element may include a graspable non-adhesive portion.

In various embodiments, the apparatus may further include a retaining band attached to the non-adhesive surface of the adhesive body, wherein, when in the rest mode, the retaining band at least partially envelopes the side element. In various embodiments, a first surface area of the first adhesive surface may be greater than a second surface area of the second adhesive surface. In various embodiments, the side element may be configured to rotate about a joint that connects the side element to the adhesive body, and the second adhesive surface may be configured to adhere to the non-adhesive surface of the adhesive body.

There is also provided a computing device comprising a flexible body comprising a first adhesive surface, a sensor connected to the flexible body, and a side element connected to the flexible body, the side element comprising a second adhesive surface having a higher bond strength than the first adhesive surface.

In various embodiments, the sensor may be configured to change operating modes when the second adhesive surface is adhered to the non-adhesive surface of the flexible body.

There is also provided a method for using an adhesive patch that includes a side element. The method comprises adhering, to an area of an object, an adhesive body of the adhesive patch, separating, from a non-adhesive surface of the adhesive body, an adhesive surface of the side element, adhering the adhesive surface of the side element to a separate area of the object, and separating the adhesive body from the object when the adhesive surface of the side element is adhered to the object.

In various embodiments, the method may further comprise a step of rotating the side element about a joint between the adhesive body and the side element, the joint comprising a pre-cut region that reduces bend resistance at the joint. In various embodiments, a non-adhesive portion of the side element may face away from the object when the adhesive body is adhered to the area of the object. In various embodiments, the non-adhesive portion of the side element may face toward the object when the adhesive surface of the side element is adhered to the separate area of the object. In various embodiments, the method may further comprise a step of re-adhering the adhesive body to the object and adhering the adhesive surface of the side element to the non-adhesive surface of the adhesive body.

The term "controller" is used herein generally to describe various apparatus relating to the operation of one or more components described herein. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

Figure 1A:
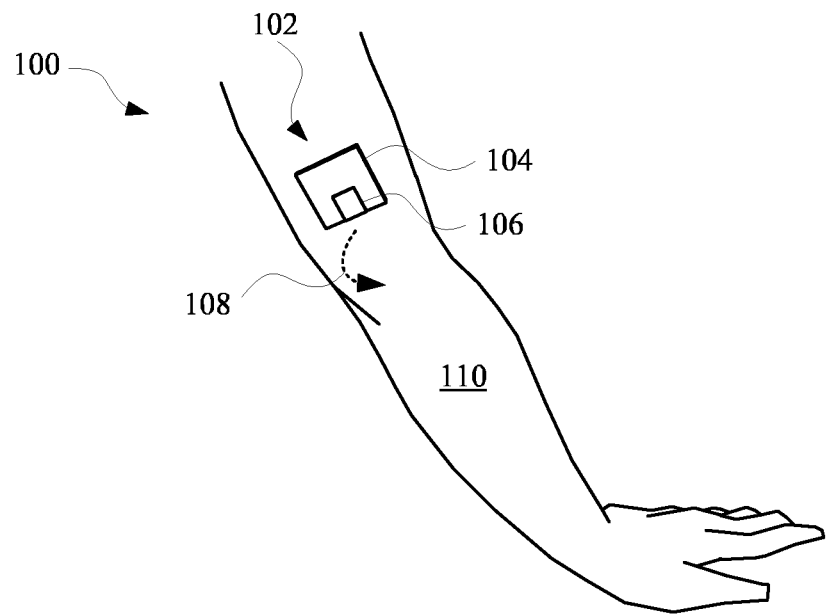
FIGS. 1A and 1B illustrate an embodiment of a sensor patch that is adhered to an appendage in a rest mode and a lift mode, respectively.

The described embodiments relate to a sensor patch for attaching to a person's body. The sensor patch can include different adhesive features that allow the sensor patch to be held in place while a portion of the sensor patch is lifted away from the body. This allows for maintenance to be performed under the sensor patch without having to entirely replace the sensor patch. Typically, when a patch is worn by a person at home or in a hospital, the skin underneath the skin should be cleaned and treated with a skin medication, otherwise the skin can become irritated and infected. In some cases, patches are removed and discarded to reduce the time needed to for performing maintenance on the skin under the patch. Furthermore, a person that is replacing the patch themselves may have issues with dexterity and eyesight, and therefore may not replace the patch in the same location prescribed by their healthcare provider. For example, a patch may need to be placed back at a specific area to allow the skin to heal, or a patch with a sensor may need to be placed back at the same location to allow the sensor to detect certain conditions.

The embodiments set forth herein resolve these issues of patch maintenance by providing a patch with adhesive side elements that can be engaged during maintenance and disengaged when maintenance is not being performed. For example, the side elements can be temporarily extended from the patch and adhered to the skin of a person, thereby arranging the patch into a lift mode. While in the lift mode, the patch can then be lifted from the skin for maintenance and then returned to the skin without losing placement and orientation of the patch on the skin. Once the patch is returned to the skin, the side elements can be removed from the skin and adhered to the patch, or otherwise re-engaged with the patch, thereby arranging the patch into a rest mode. In the rest mode, the side elements can be arranged such that non-adhesive surfaces of the side elements face away from an adhesive surface of the patch that is adhered to the skin. The patch can further include a non-adhesive liner that is initially attached to the patch before the patch is applied to the skin. Non-adhesive liners can cover an adhesive surface of the patch as well as one or more adhesive surfaces of the side elements of the patch.

The adhesives used on the patch can include at least one of a conductive and/or non-conductive adhesive. A conductive adhesive can serve as a medium for signals to travel to and/or from a sensor of the patch. The patch can include a battery that can be replaced when the patch is in the lift mode. In some embodiments, the adhesive can include a hydrogel, an adhesive foam, a latex-based adhesive, a silicon-based adhesive, a pressure-sensitive adhesive, and/or any other suitable adhesive for adhering an object to skin. In some embodiments, the bond strength of the adhesive on a side element of the patch is based on a surface area of a body of the patch. In this way, because a bond strength of the body of the patch can depend on surface area, one can ensure that the bond strength of the side element will be higher than that of the body. This allows the side element to secure the patch in place when the body of the patch is being removed from a surface.

In some embodiments, the patch can include one or more side elements extending from an edge of a body of the patch. The side element can include an adhesive surface and a non-adhesive surface. The patch can be in a rest mode when the side element is folded about a joint that connects the side element and the body of the patch. When in the rest mode, the side element can be further folded such that an adhesive surface of the side element is adhered to a surface of the patch that faces away from an adhesive surface of the body of the patch. A non-adhesive surface of the side element can face away from the adhesive surface of the body of the patch in order to prevent the patch from sticking to clothes or other objects that may contact the patch.

In other embodiments, the patch can include a side element that can be transitioned from a rest mode into a lift mode by pulling on an edge or lip of the side element in a single direction and adhering the side element to the object that the patch is adhered to. The side element can be attached to a portion of the patch that is offset from the perimeter of the patch. The side element can include a fold between two adhesive surfaces of the side element and a fold between a non-adhesive surface and an adhesive surface of the side element. The adhesive surfaces of the side element can be adhered to the same object as the patch in the lift mode, and the non-adhesive surface can extend over a portion of the patch in the lift mode. In the rest mode, the side element can be folded such that one adhesive surface of the side element is adhered to a non-adhesive surface of the side element, and another adhesive surface of the side element can be adhered to a body of the patch. The side element can include a graspable lip that can extend over an edge of the body of the patch when the side element is in the rest mode in order to allow for an easier transition between the rest mode and the lift mode.

In yet other embodiments, the patch can include a pocket on a surface of the body of the patch that faces away from an adhesive surface of the patch. The pocket can at least partially envelope a side element when the patch is in the rest mode. In this way, the side element can be limited in movement and prevented from unintentionally unfolding when in the rest mode. Transitioning the patch into the lift mode can be performed by pulling the side element out of the pocket and adhering an adhesive surface of the side element to an object that the patch is adhered to. The side element can be placed into the pocket by removing the adhesive surface of the side element from the object and inserting at least a portion of the side element back into the pocket. The adhesive surface of the side element can then be adhered to a surface of the patch while at least a portion of the side element is enveloped by the pocket. The side element can be made from a flexible and/or elastic material. For example, the side element can be made from a shape-memory material that can be pulled out of the lift mode and automatically returned to a pre-determined shape.

A patch can include one or more side elements, as well as one or more handles that can be gripped to assist with lifting of the patch when the side elements are engaged with the skin. The handle can extend over any portion of the patch such as, but not limited to a portion of a perimeter of the patch and/or an interior surface of the patch that is separate from an edge of the patch. In some embodiments, the handle can at least partially overlap the side element in the rest mode and/or the lift mode in order to stabilize the side element when operating in the rest mode and/or the lift mode.

FIG. 1A illustrates a perspective view 100 of an embodiment of a sensor patch 102 adhered to an appendage 110 in a rest mode of the sensor patch 102. The sensor patch 102 can include a sensor for collecting data related to a person's health. The sensor patch 102 can be a computing device that includes a power source and/or a controller for powering and controlling the sensor of the sensor patch 102. The sensor patch 102 can also include a transmitter for transmitting data that is based on signals from the sensor of the sensor patch 102. The sensor, transmitter, power source, and/or controller can be located in a body 104 of the sensor patch 102 and/or in remote location from the sensor patch 102. The sensor patch 102 can also include a side element 106. The side element 106 can be connected at any portion of the sensor patch 102 such as a perimeter edge or surface of the sensor patch 102. The side element 106 can include at least one adhesive surface and at least one non-adhesive surface. The adhesive surface of the side element 106 can be adhered to a non-adhesive exterior surface of the body 104 of the sensor patch 102 while the sensor patch 102 is in the rest mode. Additionally, the non-adhesive surface of the side element 106 can face away from the body 104 when in the rest mode, in order to prevent the side element 106 from sticking to clothing or other objects that can come into contact with the sensor patch 102. The sensor patch 102 can be transitioned into a lift mode by pulling the side element 106 with a pulling force in a direction 108 away from the body 104. The adhesive surface of the of the side element 106 can then be adhered to a location on the appendage 110 that is separate from an area that the body 104 is adhered to, as shown in FIG. 1B.

Figure 1B:
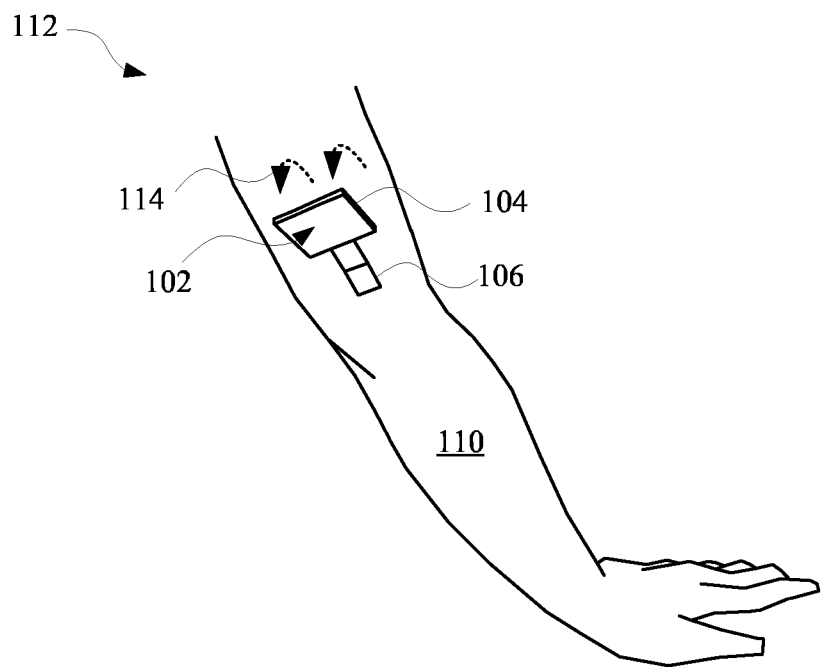

FIG. 1B illustrates a perspective view 112 of an embodiment of the sensor patch 102 in the lift mode. In the lift mode, an adhesive surface of the side element 106 is adhered to the appendage 110 of a user of the sensor patch 102. The body 104 of the sensor patch 102 can then be lifted away from the appendage 110 by a pulling force that is in a direction 114 away from the appendage 110. The area where the body 104 of the sensor patch 102 was previously adhered can then undergo some amount of maintenance including, for example, cleaning and/or sanitizing. Once the maintenance has been performed, the body 104 of the sensor patch 102 can then be adhered back onto the appendage 110 and the side element 106 can be folded on itself. For example, the side element 106 can include a fold between the adhesive surface and the non-adhesive surface of the side element 106. The adhesive surface of the side element 106 can be rotated around the fold, and the side element 106 can then be rotated such that the adhesive surface contacts and adheres to an exterior surface of the body 104. In some embodiments, when the adhesive surface is adhered to an exterior surface of the body 104 of the sensor patch 102, the sensor patch 102 is in a rest mode. Furthermore, in some embodiments, the controller of the sensor patch 102 can change an operating mode of the sensor depending on whether the sensor patch 102 is in the lift mode or the rest mode. For example, the controller can operate the sensor in a low power mode when the sensor patch 102 is in the lift mode. In some embodiments, when the sensor patch 102 is in the lift mode, data from the sensor can be discarded or invalidated in order to ensure that only data that is collected during the rest mode is kept. In other embodiments, the controller that is connected to the sensor can record timestamps. A start time stamp or a lift time stamp can be assigned to sensor data that is received when the sensor patch 102 is in the lift mode, and an end time stamp or rest time stamp can be assigned to the sensor data when the sensor patch is in the rest mode. Furthermore, sensor data received between the start time stamp and end time stamp can be discarded because the sensor data was received when the sensor patch 102 was lifted.

Figure 2A:
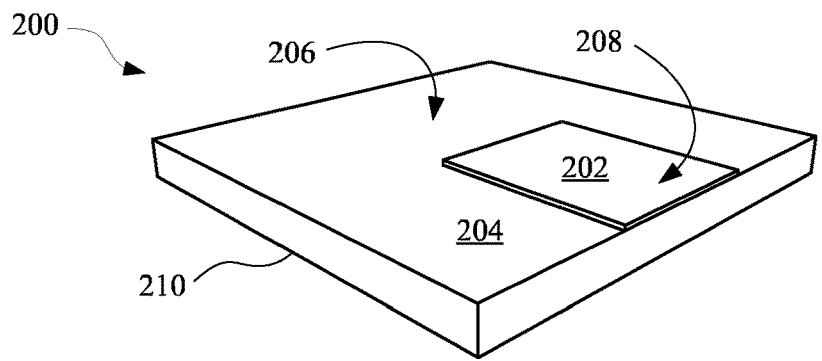
FIGS. 2A-2C illustrate perspective views of a sensor patch being transitioned from a rest mode to a lift mode according to some embodiments.
Figure 2B:
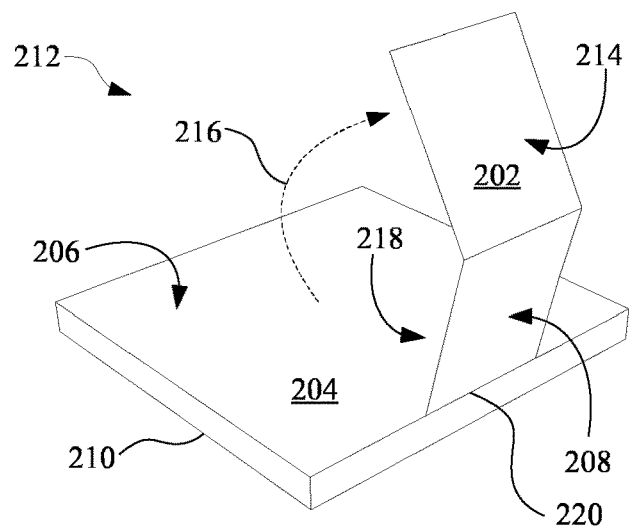
Figure 2C:
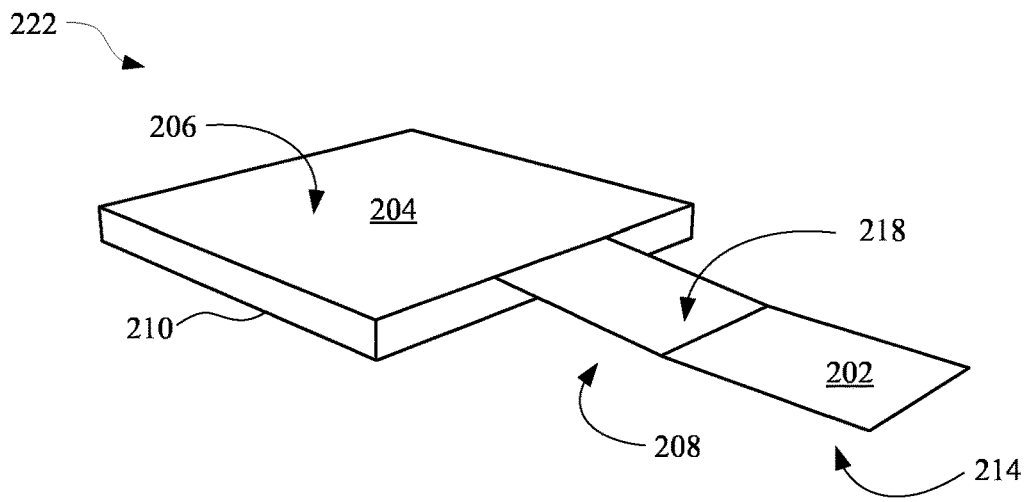

FIGS. 2A-2C illustrate perspective views of a sensor patch 210 being transitioned from a rest mode to a lift mode according to some embodiments discussed herein. Specifically, FIG. 2A illustrates a perspective view 200 of an embodiment of the sensor patch 210 in the rest mode. The sensor patch 210 can include a side element 202 and a body 204. When in the rest mode, the side element 202 can be adhered to an exterior surface 206 of the body 204. The side element 202 can be adhered to the exterior surface 206 using a chemical adhesive, a mechanical fastener such as Velcro, and/or any other type of securing apparatus. The exterior surface 206 can be a non-adhesive surface in order to prevent other objects, such as clothing or dust, from sticking to the sensor patch 210. A non-adhesive surface 208 of the side element 202 can face away from the body 204 when the sensor patch 210 is in the rest mode.

FIG. 2B illustrates a perspective view 212 of the sensor patch 210 being transitioned from the rest mode into the lift mode. When transitioning the sensor patch 210 into the lift mode, the side element 202 is forced in a direction 216 away from the exterior surface 206 of the body 204 of the sensor patch 210 and around a joint 220 between the side element 202 and sensor patch 210. Additionally, when transitioning the sensor patch 210 into the lift mode, a first surface 214 of the side element 202 is separated from a second surface 218 of the side element 202. It should be noted that the second surface 218 is a surface of the side element 202 that faces away from the non-adhesive surface 208. The first surface 214 and/or the second surface 218 can be an adhesive surface. For example, the first surface 214 can be an adhesive surface that can be adhered to an object such as an appendage when the sensor patch 210 is in the lift mode. In some embodiments, both the first surface 214 and the second surface 218 can be adhesive surfaces. Furthermore, the first surface 214 can include an adhesive that has a higher bond strength than an adhesive located on the body 204 of the sensor patch 210.

Figure 3A:
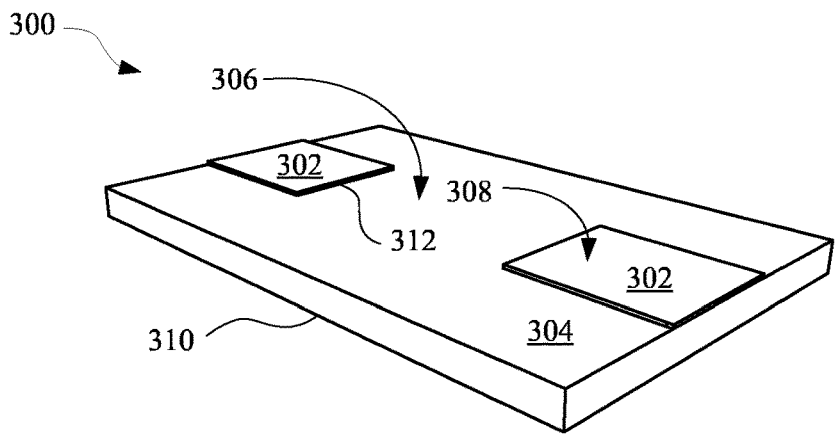
FIGS. 3A-3C illustrate an embodiment of a sensor patch that includes at least one side element having multiple folded regions for transitioning the sensor patch between a rest mode and a lift mode.
Figure 3B:
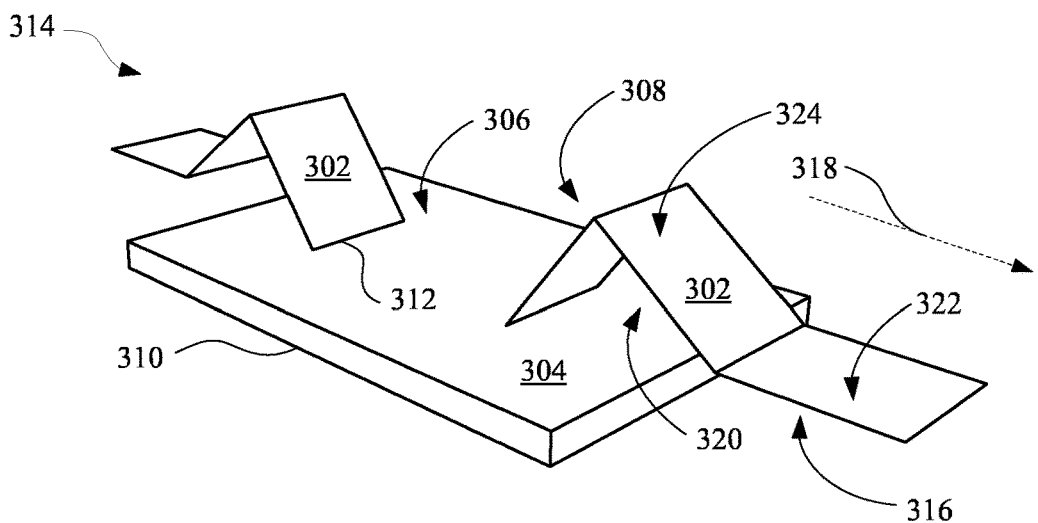
Figure 3C:
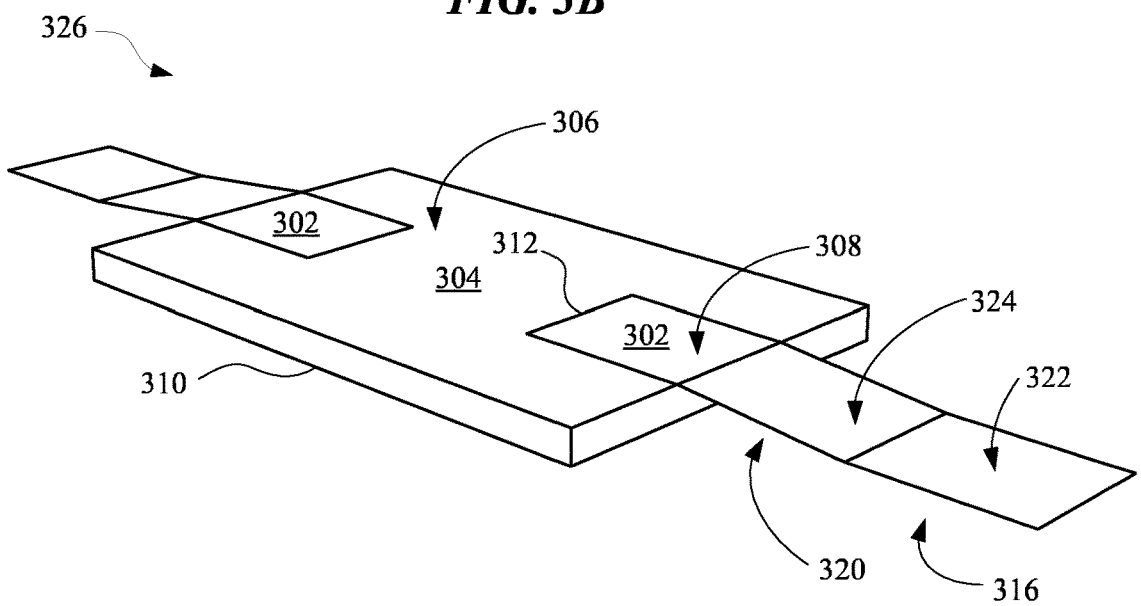

FIG. 2C illustrates a perspective view 222 of the sensor patch 210 in the lift mode. In the lift mode, the body 204 of the sensor patch 210 can be lifted from an area of an object while the side element 202 is adhered to a different area of the object. In this way, when the object is skin of an appendage, maintenance can be performed on the skin while the body 204 of the sensor patch 210 is lifted away from the skin. This promotes reusability of the sensor patch 210 and allows for more frequent maintenance of the sensor patch 210. FIGS. 3A-3C illustrate an embodiment of a sensor patch 310 that includes at least one side element having multiple folded regions for transitioning the sensor patch 310 between a rest mode and a lift mode. Specifically, FIG. 3A illustrates a perspective view 300 of the sensor patch 310 in the rest mode and each side element 302 is extending over an exterior surface 306 of the sensor patch 310. Each side element 302 can be attached to the exterior surface 306 at a joint 312 that is located within a perimeter edge of the exterior surface 306. Each side element 302 can include a non-adhesive surface 308 that faces away from the exterior surface 306 of a body 304 of the sensor patch 310. In some embodiments, a portion of each side element 302 is flush with an edge of the body 304 when the sensor patch 310 is in the rest mode. In other embodiments, a portion of the side element 302 extends over the edge of the body 304 in order to facilitate gripping of the side element 302 in the rest mode.

FIG. 3B illustrates a perspective view 314 of the sensor patch 310 transitioning into the lift mode from the rest mode. The sensor patch 310 can be transitioned into the lift mode by pulling each side element 302 in a direction 318 that is away from the body 304 of the sensor patch 310. When the side element 302 is pulled out of the rest mode, a first surface 316 of the side element 302 is removed from the exterior surface 306 of the body 304 of the sensor patch 310. Additionally, a second surface 320 of the side element 302 can be adhered to another surface of the side element 302 when in the rest mode and attached to an object when in the lift mode. It should be noted that the second surface 320 is a surface on the side element 302 that is opposite a third surface 324. Furthermore, when in the rest mode, the third surface 324 can abut a fourth surface 322. In some embodiments, the first surface 316, the second surface 320, third surface 324 and/or the fourth surface 322 can include a chemical adhesive or mechanical attachment apparatus. In other embodiments, the first surface 316, the second surface 320, the third surface 324 and/or the fourth surface 322 can be a non-adhesive surface 308.

FIG. 3C illustrates a perspective view 326 of the sensor patch 310 in the lift mode. When in the lift mode, the first surface 316 can be adhered to a location on an object that is different from an area on which the body 304 of the sensor patch 310 was adhered to in the rest mode. In some embodiments, the second surface 320 can also be adhered to the object when in the lift mode. In other embodiments, the second surface 320 is not adhered to the object when in the lift mode. When in the lift mode, a surface that is opposite the non-adhesive surface 308 can be adhered to the exterior surface 306 by attaching the non-adhesive surface 308 to an adhesive portion of the exterior surface 306. The body 304 of the sensor patch 310 can include an adhesive surface that is on an opposite side of the exterior surface 306. The adhesive on the body 304 can have a lower bond strength than another adhesive on the first surface 316. However, in some embodiments, the adhesive on the body 304 can have an equal or greater bond strength than the other adhesive on the first surface 316. In some embodiments, the first surface 316 and/or a portion of the exterior surface 306 can include Velcro loops or hooks. In other embodiments, the third surface 324 and/or the fourth surface 322 can include Velcro hooks and/or loops.

Figure 4A:
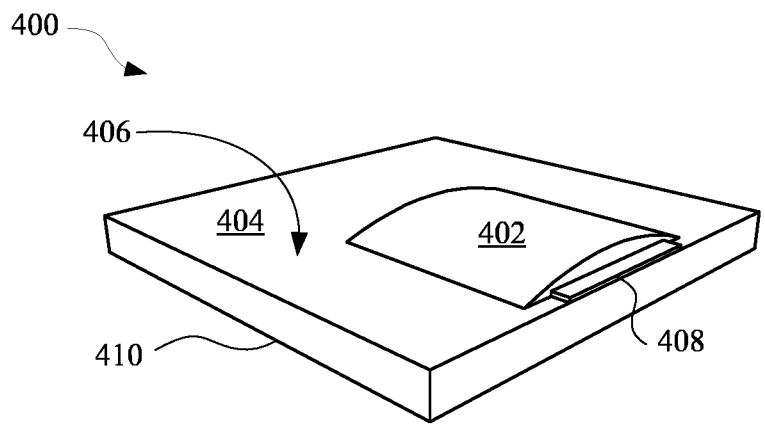
FIGS. 4A-4C illustrate an embodiment of a sensor patch that includes a retaining band that protects a side element of the sensor patch.
Figure 4B:
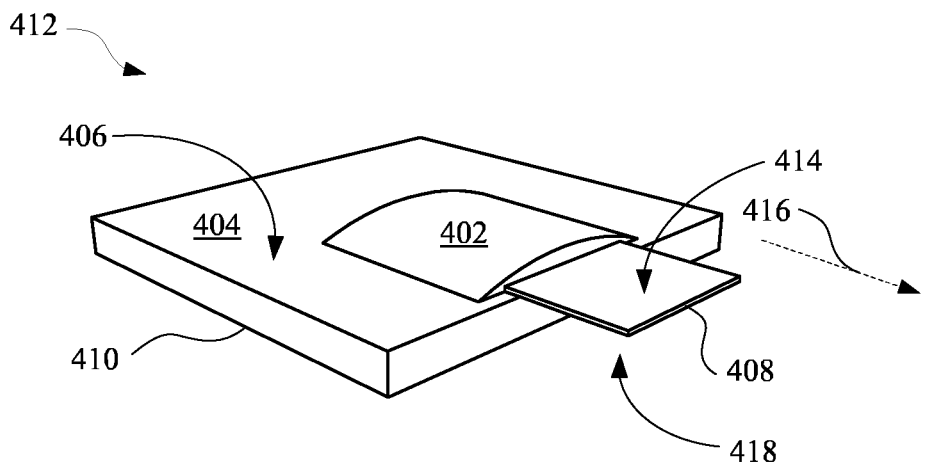
Figure 4C:
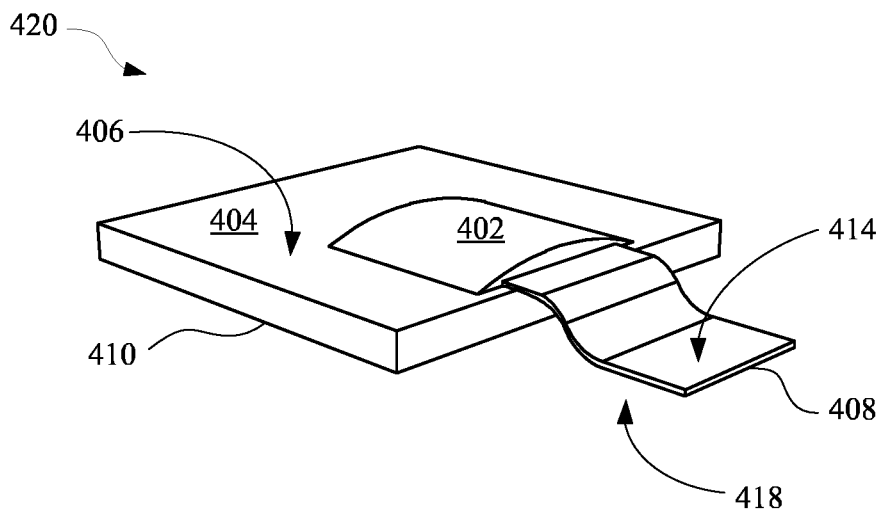

FIGS. 4A-4C illustrate an embodiment of a sensor patch 410 that includes a protection band 402 that protects a side element 408. The protection band 402 can be made from any material suitable for protecting an object from contacting other objects. The protection band 402 can connect to the exterior surface 406 at different edges of the exterior surface 406 or at different locations within a perimeter of the exterior surface 406. When in a rest mode, as illustrated in the perspective view 400 of FIG. 4A, the side element 408 is at least partially retained by or at least partially enveloped by the protection band 402. In some embodiments, a portion of the side element 408 can extend out of the protection band 402 to help facilitate removal the side element 408 from the protection band 402.

FIG. 4B illustrates a perspective view 412 of the sensor patch 410 being transitioned from the rest mode into the lift mode. The sensor patch 410 can be transitioned from the rest mode to the lift mode by pulling on the side element 408 in a direction 416 that is away from the body 404 of the sensor patch 410. The side element 408 can include an elastic material in some embodiments, in order to allow the side element 408 to be stretched in and out of the body 404 of the sensor patch 410. A portion of the side element 408 can be attached to the protection band 402 and/or the body 404 in order to secure the side element 408 to the sensor patch 410. The side element 408 can include a first surface 414 that can include a non-adhesive, and a second surface 418 that can include an adhesive surface. The second surface 418 can be attached to the exterior surface 406 when the sensor patch 410 is in the rest mode. When transitioning the sensor patch 410 into the lift mode, the second surface 418 can be at least partially removed from the exterior surface 406 and adhered to an area of an object adjacent to where the body 404 is adhered.

FIG. 4C illustrates a perspective view 420 of the sensor patch 410 in the lift mode. While in the lift mode, the side element 408 can be adhered to an area of object that is different from an area where the body 404 of the sensor patch 410 was adhered. This allows the body 404 to be lifted from the object in order that maintenance can be performed on the object. Once the maintenance is complete, the body 404 can be adhered to the area where the body 404 was previously adhered and the side element 408 can be placed back into the protection band 402. In some embodiments, a controller that controls the sensor of the sensor patch 410 can provide a signal when the body 404 of the sensor patch 410 has been removed from the object for a programmed period of time. The signal can be associated with a warning signal that warns a user of the sensor patch 410 that the body 404 should be adhered to the object again so that the sensor can continue to provide signals based on sensing properties of the object. The signal can be used by the controller to provide a feedback signal to an output device of the controller, such as a speaker, display, light, haptic feedback device, thermoelectric device, and/or any other device suitable for providing feedback to a user. The controller can output the signal in response to the body 404 being lifted from the object, the side element 408 being removed from the protection band 402, and/or the side element 408 being at least partially removed from the exterior surface 406.

Figure 5A:
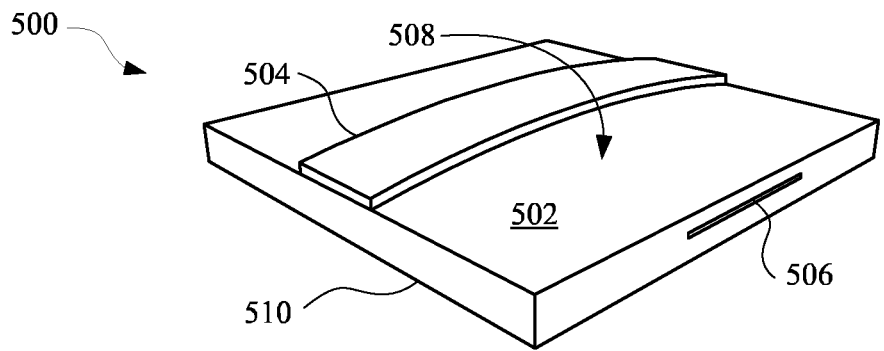
FIGS. 5A-5C illustrate an embodiment of a sensor patch that includes a strap for gripping the sensor patch when pulling a body of the sensor patch away from an object.
Figure 5B:
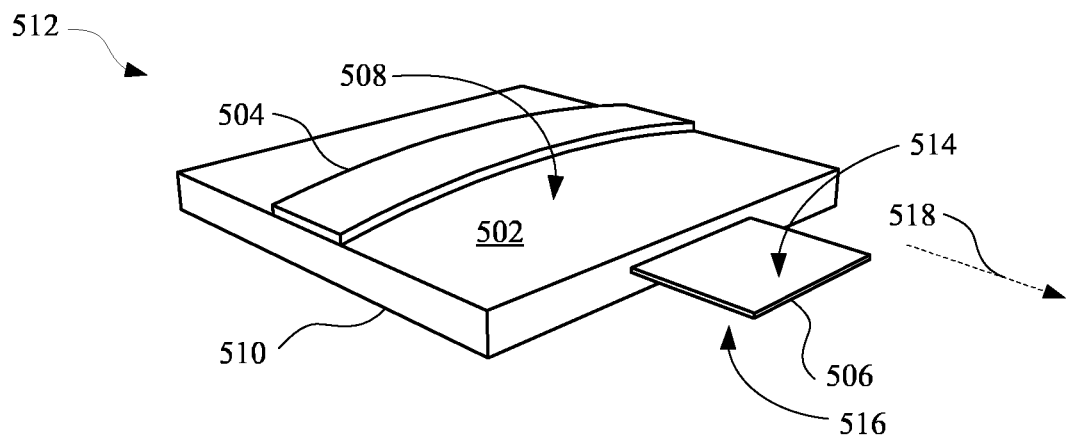
Figure 5C:
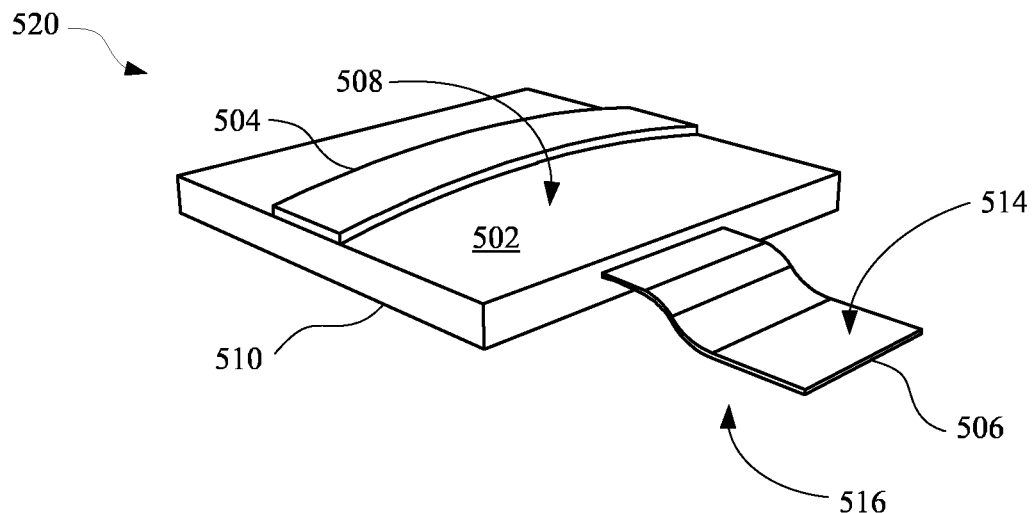

FIGS. 5A-5C illustrate an embodiment of the sensor patch 510 that includes a strap 504 for gripping the sensor patch 510 when pulling the body 502 of the sensor patch 510 away from an object. The strap 504 can be attached to edges of the body 502 of the sensor patch 510 or to a portion of an exterior surface 508 that is displaced from the edge of the body 502. In FIG. 5A, a perspective view 500 is provided to illustrate the sensor patch 510 in a rest mode where a side element 506 of the sensor patch 510 is at least partially enveloped by the body 502 of the sensor patch 510. In the rest mode, the side element 506 can be located within a pocket that is formed in the body 502 of the sensor patch 510 in order to hide the side element 506. By hiding the side element 506, any adhesive located on the side element 506 can be prevented from contacting other objects or surfaces that can come into contact with the sensor patch 510 when the sensor patch 510 is in the rest mode.

FIG. 5B illustrates a perspective view 512 of the sensor patch 510 transitioning into the lift mode from the rest mode illustrated in FIG. 5A. The sensor patch 510 can be transitioned into the lift mode by pulling on the side element 506 in a direction 518 that is away from the body 502. As a result of pulling on the side element 506, the side element 506 can extend out from the body 502 to reveal a first surface 514 and a second surface 516. The first surface 514 can be a non-adhesive surface and the second surface 516 can include an adhesive surface. The strap 504 can be held during the transition in order to hold the sensor patch 510 in place on the surface of an object such as an appendage. In some embodiments, the strap 504 can serve as the protection band 402 illustrated in FIGS. 4A-4C. Moreover, it should be noted that any feature of the any of the embodiments discussed herein can be interchanged with each other to create other embodiments. For example, the strap 504 can be included on any of the embodiments discussed herein including sensor patch 102, sensor patch 210, sensor patch 310, and/or sensor patch 410.

FIG. 5C illustrates a perspective view 520 of the sensor patch 510 in the lift mode where the second surface 516 of the side element 506 is adhered to a different area of an object than the body 502 of the sensor patch 510. In the lift mode, the body 502 can be lifted from the surface of the object. When the side element 506 is made of an elastic material, the side element 506 can act to pull on the body 502 such that less force is necessary to pull the body 502 from the surface. The sensor patch 510 can be returned to the rest mode by disconnecting the second surface 516 from the area of the object it is connected to and moving the side element 506 back into the body 502. In some embodiments, a controller located inside the body 502 can determine when the side element 506 is in or out of the body 502 and can change an operating mode of the sensor based on the arrangement of the side element 506. For example, the sensor can operate in a low power mode when the side element 506 is adhered to the surface of an object and in a normal power mode when the side element 506 is moved back into the body 502.

Figure 6:
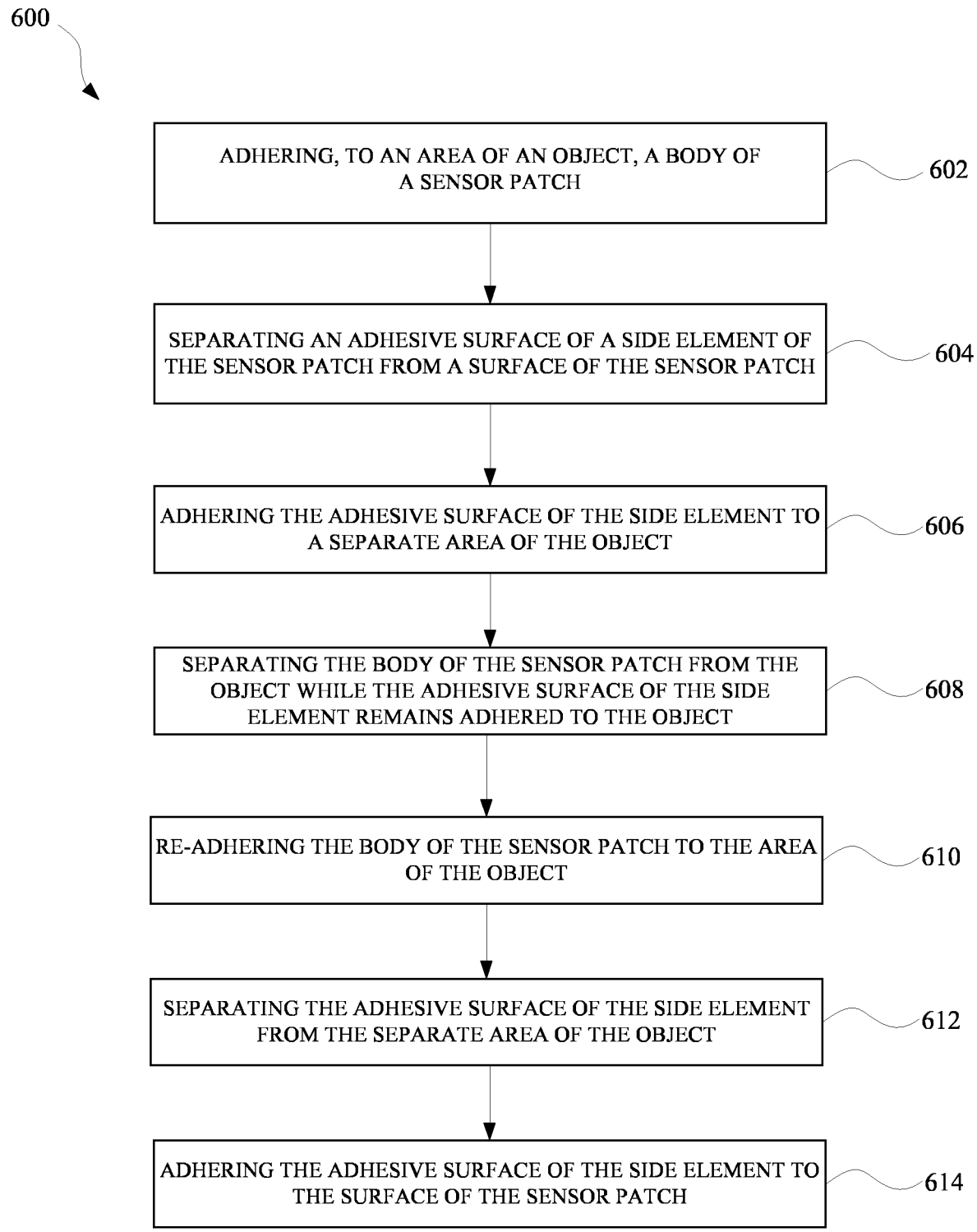
FIG. 6 illustrates a method for transitioning a sensor patch from rest mode into a lift mode, according to some embodiments.

FIG. 6 illustrates a method 600 for transitioning a sensor patch from rest mode into a lift mode, according to some embodiments. As shown, the method 600 begins at block 602, where a body of a sensor patch is adhered to an area of an object, such as an appendage of a person. At block 604, an adhesive surface of a side element of the sensor patch is separated from a surface of the body of the sensor patch. At block 606, the adhesive surface of the side element is adhered to a separate area of the object. At block 608, the body of the sensor patch is separated from the object while the adhesive surface of the side element remains adhered to the object. In this way, maintenance can be performed on the object while the body of the sensor patch is separated from the object. Additionally, the body of the sensor patch can be adhered to the object at the previous location of the object because the side element serves as a placeholder for the sensor patch. At block 610, the body of the sensor patch is re-adhered to the area of the object. At block 612, the adhesive surface of the side element can separated from the separate area of the object. At block 614, the adhesive surface of the side element can be adhered to the surface of the body of the sensor patch.

Figure 7:
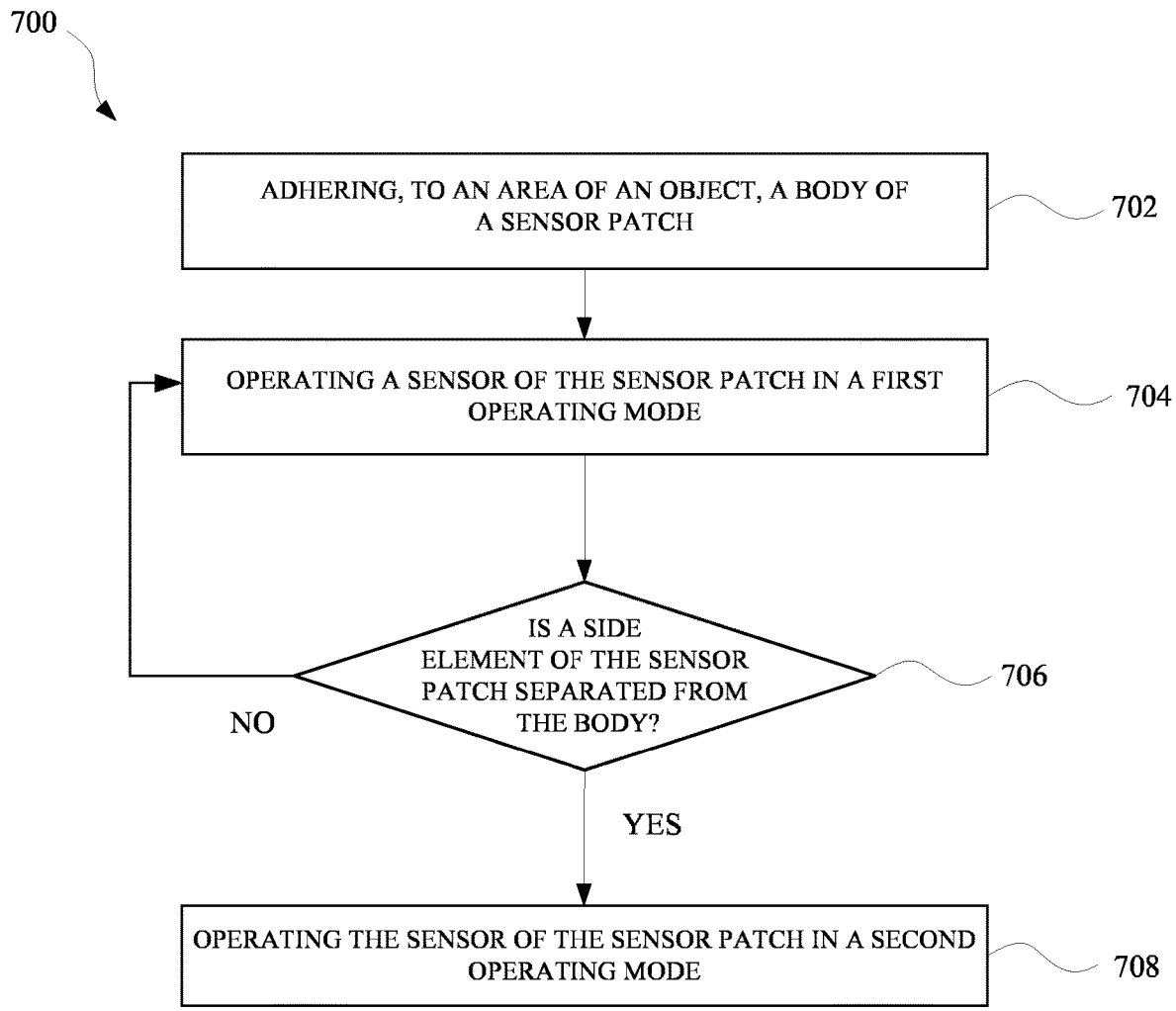
FIG. 7 illustrates a method for controlling a sensor of a sensor patch based on whether the sensor patch is in a lift mode or a rest mode, according to some embodiments.

FIG. 7 illustrates a method 700 for controlling a sensor of a sensor patch based on whether the sensor patch is in a lift mode or a rest mode, according to some embodiments. As shown, the method 700 begins at block 702, where the body of the sensor patch is adhered to an area of an object. At block 704, the sensor of the sensor patch is operated in a first operating mode. The first operating mode can be a regular power mode where the sensor is outputting a signal based on a physical property of the object. At block 706, a determination is made whether a side element of the sensor patch is separated from the body of the sensor patch. The determination can be made by a controller of the sensor patch, a contact switch of the sensor patch, and/or any other circuit element capable of indicating a change in placement of a sensor. If, at block 706, the side element of the sensor patch is separated from the body, then the method 700 proceeds to block 708 where the sensor of the sensor patch is operated in a second operating mode. The second operating mode can be a low power mode where the sensor is not providing a signal, or the sensor is providing a lower power signal relative to the signal provided in the first operating mode. In some embodiments, in the second operating mode, the data of the sensor can be invalidated or discarded. For example, time stamps can be recorded when the sensor patch is lifted and when the sensor patch is returned to a rest mode. The data collected between the time corresponding to the time stamps can be discarded because the data may be inaccurate. It should be noted that a controller that is part of the sensor patch, or remote from the sensor patch, can transition the sensor between operating modes. If the side element is not separated from the body of the sensor patch, the method 700 returns to block 704 where the sensor is operated in the first power mode.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

The invention claimed is:

1. An apparatus, comprising:
   a single adhesive body that includes a first adhesive surface and a non-adhesive surface opposite the first adhesive surface, the first adhesive surface configured to adhere to an object; and
   a side element that extends from an edge of the adhesive body, the side element comprising a second adhesive surface that is configured to:
      adhere to the non-adhesive surface when in a rest mode, and
      adhere to the object when in a lift mode,
   wherein the apparatus is structured such that, in the rest mode, no edges of the side element extend beyond any edges of the non-adhesive surface of the adhesive body,
   wherein the apparatus is structured such that, in the rest mode, the only component of the apparatus that can adhere to the object is the adhesive body, and
   wherein the apparatus is structured such that, in the lift mode, the adhesive body does not adhere to the object and the only component of the apparatus that adheres to the object is the second adhesive surface.

2. The apparatus of claim 1, wherein the first adhesive surface has a lower bond strength than the second adhesive surface.

3. The apparatus of claim 1, wherein the side element includes a non-adhesive portion configured to face away from the second adhesive surface when the side element is in the rest mode.

4. The apparatus of claim 3, wherein the non-adhesive portion extends between the adhesive body and the second adhesive surface when the side element is in the lift mode.

5. The apparatus of claim 3, wherein the second adhesive surface, when in the rest mode, is configured to fold between a first portion of the second adhesive surface and a second portion of the second adhesive surface.

6. The apparatus of claim 5, wherein, when in the rest mode, the first portion of the second adhesive surface adheres to the second portion of the second adhesive surface, and a distal end of the side element includes a graspable non-adhesive portion.

7. The apparatus of claim 1, further comprising:
a retaining band attached to the non-adhesive surface of the adhesive body, wherein, when in the rest mode, the retaining band at least partially envelopes the side element.

8. The apparatus of claim 1, wherein a first surface area of the first adhesive surface is greater than a second surface area of the second adhesive surface.

9. The apparatus of claim 1, wherein the side element is configured to rotate about a joint that connects the side element to the adhesive body, and the second adhesive surface is configured to adhere to the non-adhesive surface of the adhesive body.

10. The apparatus of claim 1, further comprising:
a sensor connected to the adhesive body; and
a power source for powering the sensor and/or a controller for controlling the sensor.

11. The apparatus of claim 10, wherein the controller is configured to change operating modes of the sensor when it is determined that the second adhesive surface is adhered to the non-adhesive surface of the adhesive body.

12. A method for using an adhesive patch that includes a single adhesive body and a side element, the method comprising:
employing either a rest mode or a lift mode,
wherein employing the rest mode comprises:
adhering, to an area of an object, an adhesive surface of the adhesive body such that no components of the adhesive patch other than the adhesive body are adhered to the object; and
adhering, to a non-adhesive surface of the adhesive body, an adhesive surface of the side element such that all edges of the side element are contained within all edges of the non-adhesive surface of the adhesive body, the non-adhesive surface of the adhesive body being disposed opposite the adhesive surface of the adhesive body,
wherein employing the lift mode comprises:
separating, from the non-adhesive surface of the adhesive body, the adhesive surface of the side element;
adhering the adhesive surface of the side element to a separate area of the object; and
separating the adhesive body from the object when the adhesive surface of the side element is adhered to the object.

13. The method of claim 12, wherein employing the lift mode further comprises a step of:
rotating the side element about a joint between the adhesive body and the side element, the joint comprising a pre-cut region that reduces bend resistance at the joint.

14. The method of claim 12, wherein a non-adhesive portion of the side element faces away from the object when the adhesive body is adhered to the area of the object and wherein the non-adhesive portion of the side element faces toward the object when the adhesive surface of the side element is adhered to the separate area of the object.

15. The method of claim 12, further comprising a step of transitioning from employing the lift mode to employing the rest mode, the transitioning comprising:
after the separating the adhesive body from the object, re-adhering the adhesive body to the object; and
adhering the adhesive surface of the side element to the non-adhesive surface of the adhesive body such that all edges of the side element are contained within all edges of the non-adhesive surface of the adhesive body.

* * * * *